United States Patent [19]

Doyle

[11] Patent Number: 4,591,121
[45] Date of Patent: May 27, 1986

[54] HOSPITAL I.V. POLE ADJUNCT

[76] Inventor: Raymond E. Doyle, 13218 Ravine Trail, Fort Wayne, Ind. 46804

[21] Appl. No.: 628,521

[22] Filed: Jul. 6, 1984

[51] Int. Cl.⁴ ............................................. A47B 97/00
[52] U.S. Cl. .................................. 248/201; 248/121; 5/503
[58] Field of Search ............... 246/201, 124, 122, 251, 246/318, 125; 5/508, 503; 248/131, 145, 121

[56] References Cited

U.S. PATENT DOCUMENTS

| 828,164 | 8/1906 | Williams | 5/503 |
| 902,635 | 11/1908 | Wowra | 248/292.1 |
| 1,048,750 | 12/1912 | Smith | 5/503 |
| 4,410,158 | 10/1983 | Maffei | 5/508 |

FOREIGN PATENT DOCUMENTS 367023  2/1932  United Kingdom .................... 5/508

Primary Examiner—Reinaldo P. Machado
Assistant Examiner—Alvin Chin-Shue
Attorney, Agent, or Firm—David A. Lundy

[57] ABSTRACT

A hospital intravenous or I.V. pole adjunct for supporting I.V. fluid containers and medical devices connected to a patient in cooperation with and in transport between pairs of hospital I.V. poles. The adjunct has a rigid elongated main member with a central portion and ends. A pair of connectors are displaceably mounted to the main member. The connectors are displaceable along the main member to engage a pair of spaced I.V. poles. A plurality of retainers are displaceably mounted on the main member. The retainers support I.V. fluid containers and medical devices. A pair of stops are attached to the ends of the main member to limit the displacement of the connectors and retainers.

15 Claims, 3 Drawing Figures

HOSPITAL I.V. POLE ADJUNCT

BACKGROUND OF THE INVENTION

The present invention pertains to hospital intravenous (I.V.) supports and more particularly to a hospital I.V. pole adjunct for use in supporting the multitude of containers for palliative preparations, monitors and other hospital equipment needed for the treatment of critically ill patients.

Hospital patients have long been given intravenous (I.V.) fluids from bottles or other containers suspended from hospital I.V. poles mounted to the patient's bed, operating table or gurney or from free standing I.V. poles. The poles generally each have two arms and provision is generally made for mounting two I.V. poles, one to each side, just forward of the patient's head. In addition to I.V. fluid containers, the poles are used to support various medical devices such as arterial pressure monitors and infusion pumps which are adapted to hang from or clamp onto the I.V. poles.

The I.V. poles are adequate for most patients since most patients do not need a large number of different I.V. fluids and devices. In intensive care, in surgery and in transporting patients to and from surgery, however, the opposite is often the case. A cardiac intensive care patient, for example, might need separate I.V.s for blood, dopamine, nitroprusside, hyperalimentation fluid, antibiotics, and an insulin drip in addition to monitors and other devices. In that situation, a nest of intravenous fluid tubing is created which obscures the view of monitors and devices on the I.V. poles, decreases the efficiency of nursing procedures and creates a danger of confusion regarding the various I.V. fluids. Additional free standing I.V. poles may be used to alleviate this problem to some extent, however, such freestanding I.V. poles are not practical while the patient is being transported, are relatively expensive to maintain at all locations in the hospital where they might be needed, and are cumbersome to maneuver around a bed occupied by a critically ill patient.

I.V. poles have the additional shortcoming that I.V. fluid containers and medical devices must be individually removed and transferred to other I.V. poles or carried in hand, when the patient or the I.V. poles are moved. This shortcoming is serious, for example, where a patient has stopped breathing and must be resuscitated, intubated and placed on a respirator, since it is desirable to maintain the patient's airway from a position superior to the patient's head after first removing the I.V. poles and headboard of the patient's bed.

It is therefore highly desirable to provide an improved hospital I.V. pole adjunct.

It is also highly desirable to provide an improved hospital I.V. pole adjunct that can easily support a large number of intravenous fluid containers and medical devices.

It is yet highly desirable to provide an improved hospital I.V. pole adjunct that can be easily connected to a pair of I.V. poles.

It is further highly desirable to provide an improved hospital I.V. pole adjunct which can be easily removed from a pair of I.V. poles and transported by a person when a large number of I.V. fluid containers and medical devices are attached to the hospital I.V. pole adjunct and to a patient.

It is yet further highly desirable to provide an improved hospital I.V. pole adjunct which is readily sterilized by autoclaving.

It would finally be highly desirable to provide an improved I.V. pole adjunct which has all of the above desired features.

SUMMARY OF THE INVENTION

It is an object of the invention to provide an improved hospital I.V. pole adjunct.

It is another object of the invention to provide an improved hospital I.V. pole adjunct that can easily support a large number of intravenous fluid containers and medical devices.

It is yet another object of the invention to provide an improved hospital I.V. pole adjunct that can be easily connected to a pair of I.V. poles.

It is still another object of the invention to provide an improved hospital I.V. pole adjunct which can be easily removed from a pair of I.V. poles and transported by a person when a large number of I.V. fluid containers and medical devices are attached to the hospital I.V. pole adjunct and to a patient.

Yet another object of the invention to provide an improved hospital I.V. pole adjunct which can be readily sterilized by autoclaving.

Still a further object of the invention to provide an improved hospital I.V. pole adjunct which has all of the above desired features.

In the broader aspects of the invention there is provided a hospital I.V. pole adjunct for supporting I.V. fluid containers and medical devices connected to a patient in cooperation with and in transport between pairs of I.V. poles. The hospital I.V. pole adjunct has a rigid elongated main member with a central portion and ends. A pair of connectors are displaceably mounted to the main member and displaceable along the main member to engage a pair of I.V. poles. A plurality of retainers are displaceably mounted on the main member to support I.V. fluid containers and medical devices. A pair of stops are attached to the ends of the main member to limit the displacement of the connectors and retainers.

BRIEF DESCRIPTION OF THE DRAWINGS

The above-mentioned and other features and objects of this invention and the manner of obtaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
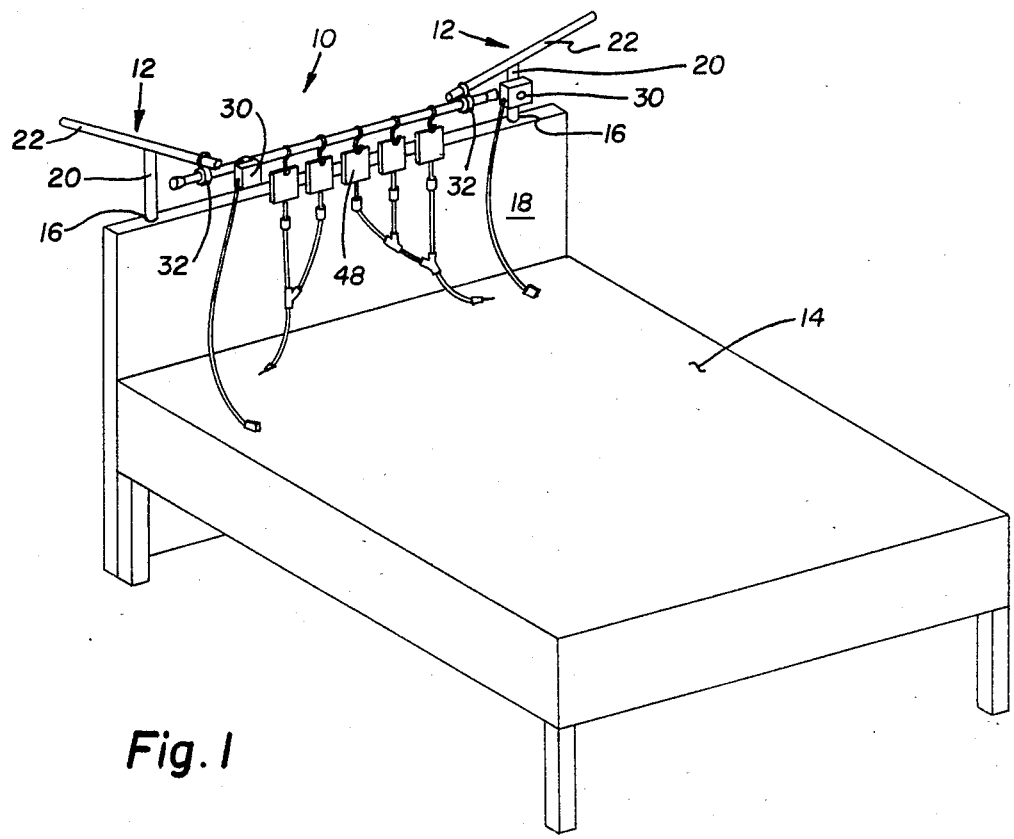
FIG. 1 is a perspective view of the hospital I.V. pole adjunct of the invention supporting a number of I.V. fluid containers and medical devices in cooperation with a hospital bed including a pair of I.V. poles.
Figure 2:
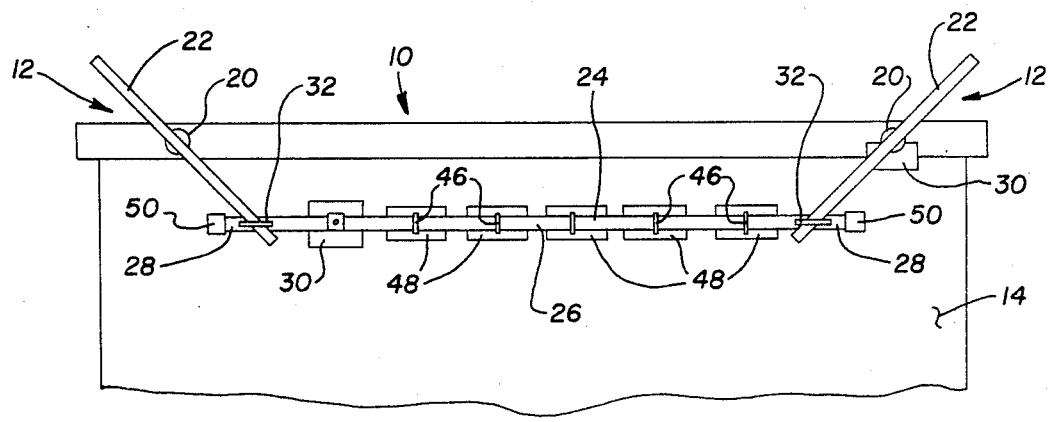
FIG. 2 is an upper plan view of the hospital I.V. pole adjunct of the invention and hospital bed of FIG. 1.
Figure 3:
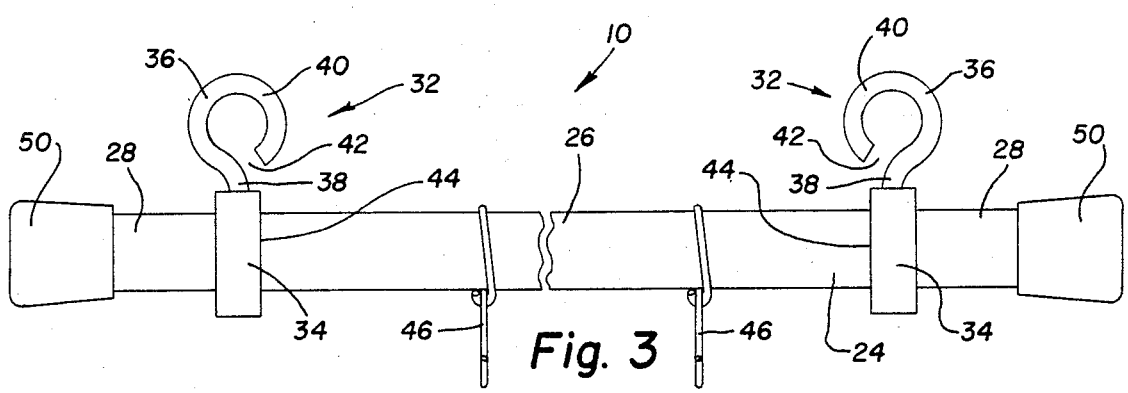
FIG. 3 is a front plan view of the hospital I.V. pole adjunct of the invention.

The hospital I.V. pole adjunct 10 of the invention is designed to be used in cooperation with a pair of spatially related I.V. poles 12 and a patient support structure 14 such as a hospital bed, gurney or operating table. The I.V. poles 12 may be freestanding, but more generally they are held by holders 16 which are attached to or are a part of the patient support structure 14. The I.V. poles 12 generally freely rotate in the holders 16. In FIG. 1, the holders 16 are a part of a headboard 18. The I.V. poles 12 generally have a vertical mast 20 and one or more arms 22 extending generally at right angles to the mast 20. The hospital I.V. pole adjunct 10 of the invention removably engages arms 22 of the I.V. poles 12.

The hospital I.V. pole adjunct 10 of the invention has an elongate main member 24. The main member 24 has a central portion 26 and ends 28. In a specific embodiment, the thickness of the main member 24 is about the same as the diameter of an I.V. pole 12 so that medical devices 30 which include a provision for attachment to an I.V. pole 12 can also be attached to the main member 24. Many medical devices 30 are provided with a screw clamp for that purpose. In another specific embodiment, the main member 24 is cylindrical in shape in addition to having the same diameter as the I.V. pole 12 so that a medical device 30 having a screw clamp can be attached to the main member 24 at any desired angle to the horizontal.

A pair of connectors 32 are mounted on the main member 24. The connectors each have a band portion 34 and a hook portion 36. Each hook portion 36 has a shank 38 and an bend 40. The hook portions 36 of the connectors 32 are recurvate and extend inwards towards the central portion 26 of the main member 24 away from the ends 28 of the main member 24. The hook portions 36 define gaps 42 which are directed toward each other and the central portion 26 of the main member 24. The gaps 42 are coplanar with the longest dimension of the main member 24.

The band portions 34 of the connectors 32 loosely surround the main member 24 and have about the same cross-sectional shape as the main member 24. The connectors 32 are displaceable along the main member 24. This permits the hospital I.V. pole adjunct 10 of the invention to be used in applications in which the spatial distance between the I.V. poles 12 may vary. The main member 24, however, is longer than the distance between the arms 22 of the pair of I.V. poles 12 with which the hospital I.V. pole adjunct 10 of the invention is used. The main member 24 is shorter than the narrowest horizontal dimension of the patient's support structure 14 with which it would be expected to be used. These limits on the length of the main member 24 in combination with the design of the connectors 32 described below provides for a stable structure which can support a large number of I.V. solution containers and medical devices without obstructing access to the patient and movement around the patient support structure 14 or movement of the patient support structure 14 as with a gurney.

The band portions 34 of the connectors 32 fit loosely on the main member 24 such that the rotation of the I.V. poles 12 supporting the hospital I.V. pole adjunct 10 of the invention is limited. Rotational movement of the arms 22 of the I.V. poles 12 in a direction away from the ends 28 of the main member 24 and toward the central portion 26 of the main member 24 causes the arms 22 to contact the bends 40 of the hook portions 36 of the connectors 32. This results in a deflection of the connectors 32 at an angle to the longest dimension of the main member 24 and forces the diagonally opposed edges 44 of the band portion 34 against the main member 24 so as to frictionally grip the main member 24, restrict the movement of the connectors 32 along the main member 24 and renders the adjunct 10 stable minimizing any jostling of the I.V. fluid containers 48. Although there may be detents on the arms 22 and motion of the connectors 32 toward each other could result in the connectors 32 coming out of the detents, slipping off the arms 22 and causing the hospital I.V. pole adjunct 10 of the invention to fall, the interaction between the connectors 32 and the main member 24 prevents the connectors 32 from easily sliding off the arm 22.

Rotational movement of the arms 22 of the I.V. poles 12 in the opposite direction, that is moving the arms away from the central portion 26 of the main member 24 and toward the ends 28 of the main member 24, moves the arms 22 against the shanks 38 of the hook portions 36 of the connectors 32 as opposed to the bends 40. This movement of the arms 22 causes the connectors 32 to move freely in a direction away from each other and the central portion 26 of the main member 24 and permits the easy mounting of the hospital I.V. pole adjunct 10 of the invention upon a pair of I.V. poles 12.

The adjunct 10 of the invention is mounted on a pair of I.V. poles 12 by rotating the I.V. poles so that the arms 22 of the I.V. poles extend over the patient's support structure 14 and are nearly as close together as possible. The hospital I.V. pole adjunct 10 of the invention is then positioned adjacent to the I.V. poles 12, the connectors 32 are pushed relatively close together along the main member 24 and the I.V. poles 12 are then each individually turned so that each respective arm 22 engages a connector 32. After this is accomplished with each I.V. pole 12, the I.V. poles 12 are rotated so as to move the arms 22 outward from the central portion 26 of the main member 24 until they can move no further. This procedure is easy since the connectors 32 move freely in a direction out from the center portion 26 of the main member 24 toward the ends 28 of the main member 24. The hospital I.V. pole adjunct 10 of the invention is then in a stable position.

A plurality of retainers 46 are displaceably mounted on the main member 24. The I.V. fluid containers 48 are supported by these retainers 46. The exact shape of the retainers 46 will be determined by the mounting needs of the I.V. fluid containers 48. In many applications it is convenient to make the retainers 46 in the shape of hooks attached to bands much like the connectors 32. The number of retainers which may be used is limited only by the space available, the size of the I.V. fluid containers 48 and medical devices 30 to be used, and the structural strength of the main member 24.

The displacement of the connectors 32 and the retainers 46 on the main member 24 is limited by a pair of stops 50 attached to the ends 28 of the main member 24. The stops 50 and the ends 28 are engageably threaded and connectors 32 and the retainers 46 can be added to or revived from the main member 24 of the hospital I.V. pole adjunct 10 of the invention upon the removal of the stops 50.

It is desirable to make the main member 24 and the other parts of the hospital I.V. pole adjunct 10 of the invention out of a strong rigid material such as stainless steel which can support as many I.V. fluid containers 48 and medical devices 30 as may be desired without risk of structural failure. In order to save weight and permit the easy transport of the hospital I.V. pole adjunct 10 of the invention when it is loaded with a number of I.V. fluid containers 48 and medical devices 30 connected to a patient, stainless steel tubing is used for the main member 24 in a specific embodiment. In all embodiments of the hospital I.V. pole adjunct 10 of the invention, the material of main member 24 must be able to withstand repeated disassembly and sterilization by autoclaving of regular hospital use.

While a specific embodiment of the invention has been shown and described herein for purposes of illustration, it is desired that the protection afforded by any patent which may issue upon this application not be limited strictly to the disclosed embodiment; but that it extend to all structures and arrangements which contain the essence of the invention and which fall fairly within the scope of the claims which are appended hereto:

What is claimed is:

1. A hospital I.V. pole adjunct for supporting I.V. fluid containers and medical devices connected to a patient in cooperation with a pair of spatially related I.V. poles and in transport to and from said I.V. poles comprising: a rigid elongated main member having a central portion and ends, a pair of connectors mounted on said main member, said connectors each having a band portion and a hook portion, said hook portion having a shank and a bend, said bend curving in the direction from said ends towards said central portion of said main member, said hook portions being engagable with said spatially related I.V. poles on a one-to-one basis, said band portions surrounding said main member, said band portions being displaceable along said main member, a plurality of supporting retainers displaceably mounted on said main member between said connectors, said retainers being supportingly connectable to I.V. fluid containers and medical devices, a pair of stops attached to said ends of said main member, said stops limiting the displacement of said connectors and said retainers along said main member.

2. The hospital I.V. pole adjunct of claim 1 wherein said main member, said connectors, said retainers, and said stops are structural stable to repetitive sterilization by autoclaving.

3. The hospital I.V. pole adjunct of claim 1 wherein said main member, said connectors, said retainers, and said stops are detachably assembled.

4. The hospital I.V. pole adjunct of claim 1 wherein said main member is cylindrical and has about the same diameter as said I.V. poles.

5. The hospital I.V. pole adjunct of claim 1 wherein said main member is tubular.

6. The hospital I.V. pole adjuct of claim 1 wherein said hook portion defines a gap, said gap being generally coplanar with the longest dimension of said main member.

7. The hospital I.V. pole adjunct of claim 1 wherein said main member has a longest dimension greater than the distance between said arms of said pair of I.V. poles.

8. The hospital I.V. pole adjunct of claim 1 wherein said band portion in cross-section has a shape geometrically similar to said main member.

9. A hospital I.V. pole adjuct for supporting I.V. fluid containers and medical devices connected to a patient, in association with or apart from a patient support structure which includes a pair of spatially related I.V. poles which have arms, said hospital I.V. pole adjunct comprising: a rigid, elongate main member having a central portion and ends, a pair of connectors displaceably mounted on said main member, said connectors each having a recurvate hook portion and a band portion, said hook portions engaging said arms of said I.V. poles on a one-to-one basis, said hook portions each having a bend and a shank, said bend being predominately engaged by a respective one of said arms during rotational movement of said respective arm in a direction toward said central portion of said main member, said shank being predominately engaged by said respective arm during rotational movement of said respective arm in a direction away from said central portion of said main member, said band portions loosely encircling said main member, said band portions being deflectable into gripping relationship with said main member, said band portions restricting movement of said connectors in a direction toward said central portion of said main member by said rotational movement of said respective arm in a direction toward said central portion of said main member and said predominant engagement of said bend of said hook by said arm, a plurality of retainers displaceably mounted on said main member, said retainers supporting said I.V. fluid containers and said medical devices, a pair of stops detachably connected to said ends of said main member to limit the displacement of said connectors and said retainers.

10. The hospital I.V. pole adjunct of claim 9 wherein said band portions of said connectors each have edges which frictionally engage said main member upon movement of said respective arm in a direction toward said central portion of said main member.

11. The hospital I.V. pole adjunct of claim 9 wherein said main member has a longest dimension greater than the distance between said arms of said pair of I.V. poles.

12. The hospital I.V. pole adjunct of claim 9 wherein said main member, said connectors, said retainers, and said stops are structural stable to repetitive sterilization by autoclaving.

13. The hospital I.V. pole adjunct of claim 9 wherein said main member, said connectors, said retainers, and said stops are detachably assembled.

14. The hospital I.V. pole adjunct of claim 9 wherein said main member is cylindrical and has about the same diameter as said I.V. poles.

15. The hospital I.V. pole adjunct of claim 9 wherein said main member is tubular.

* * * * *